US008012090B2

(12) United States Patent
Steen (10) Patent No.: US 8,012,090 B2
(45) Date of Patent: Sep. 6, 2011

(54) METHOD AND APPARATUS FOR REAL TIME ULTRASOUND MULTI-PLANE IMAGING

(75) Inventor: Eric Normann Steen, Moss (NO)

(73) Assignee: General Electric Company, Schenectady, NY (US)

( * ) Notice: Subject to any disclaimer, the term of this patent is extended or adjusted under 35 U.S.C. 154(b) by 605 days.

(21) Appl. No.: 10/925,456

(22) Filed: Aug. 25, 2004

(65) Prior Publication Data
US 2005/0283078 A1    Dec. 22, 2005

Related U.S. Application Data

(60) Provisional application No. 60/581,675, filed on Jun. 22, 2004, provisional application No. 60/583,578, filed on Jun. 29, 2004.

(51) Int. Cl.
*A61B 8/00* (2006.01)
(52) U.S. Cl. .................. 600/437; 600/407; 600/443
(58) Field of Classification Search ................ 600/437, 600/443
See application file for complete search history.

(56) References Cited

U.S. PATENT DOCUMENTS

| | | | | |
|---|---|---|---|---|
| 5,159,931 A | * | 11/1992 | Pini | 600/443 |
| 5,174,296 A | * | 12/1992 | Watanabe et al. | 600/463 |
| 5,299,577 A | * | 4/1994 | Brown et al. | 600/443 |
| 5,546,807 A | * | 8/1996 | Oxaal et al. | 73/606 |
| 5,699,805 A | * | 12/1997 | Seward et al. | 600/459 |
| 5,776,067 A | | 7/1998 | Kamada et al. | |
| 5,841,830 A | * | 11/1998 | Barni et al. | 378/15 |
| 6,036,646 A | | 3/2000 | Barthe et al. | |
| 6,099,474 A | | 8/2000 | Solek | |
| 6,171,247 B1 | * | 1/2001 | Seward et al. | 600/459 |
| 6,241,675 B1 | | 6/2001 | Smith et al. | |
| 6,245,017 B1 | * | 6/2001 | Hashimoto et al. | 600/447 |
| 6,276,211 B1 | | 8/2001 | Smith | |
| 6,436,049 B1 | | 8/2002 | Kamiyama et al. | |
| 6,607,488 B1 | | 8/2003 | Jackson et al. | |
| 6,669,641 B2 | | 12/2003 | Poland et al. | |
| 6,709,394 B2 | | 3/2004 | Frisa et al. | |

(Continued)

FOREIGN PATENT DOCUMENTS
EP    1 489 972 B1    11/2009

(Continued)

OTHER PUBLICATIONS

European Search Report dated Sep. 21, 2005, Application/Patent No. 0525 3877.4-2305 PCT, (5) references, (2) pages.

(Continued)

*Primary Examiner* — Brian Casler
*Assistant Examiner* — James Kish
(74) *Attorney, Agent, or Firm* — Dean Small; The Small Patent Law Group (57) ABSTRACT

An ultrasound system is provided that includes a probe for successively acquiring ultrasound information from an object along at least three distinct scan planes. The scan planes intersect one another along an axis extending from the probe through the object. A memory is included for storing data slices corresponding to the at least three distinct scan planes based on the ultrasound information. Also included is a processor that accesses the memory to select and obtain the data slices and generates ultrasound images based on the data slices. A display is included for co-displaying the ultrasound images.

29 Claims, 6 Drawing Sheets

U.S. PATENT DOCUMENTS

| | | |
|---|---|---|
| 6,755,786 B2 | 6/2004 | Frisa et al. |
| 6,755,788 B2 | 6/2004 | Demers et al. |
| 6,761,689 B2 | 7/2004 | Salgo et al. |
| 2003/0055308 A1 | 3/2003 | Friemel et al. |
| 2003/0216646 A1 | 11/2003 | Angelsen et al. |

FOREIGN PATENT DOCUMENTS

| | | |
|---|---|---|
| JP | 08-117236 | 5/1996 |
| JP | 2000135217 (A) | 5/2000 |
| JP | 4584586 (B2) | 11/2010 |
| WO | WO 00/58754 | 10/2000 |
| WO | WO 03/077766 A1 | 9/2003 |

OTHER PUBLICATIONS

Asbjorn Stoylen, Charlotte B. Ingul and Hans Torp; "Strain and Strain Rate Parametric Imaging"; Cardiovascular Ultrasound 2003; Aug. 2003; pp. 1-12.

Norwegian University of Science and Technology; Trondheim, Norway, Aug. 25, 2003.

* cited by examiner

METHOD AND APPARATUS FOR REAL TIME ULTRASOUND MULTI-PLANE IMAGING

CROSS REFERENCE TO RELATED APPLICATIONS

This application claims priority to and the benefit of the filing date of U.S. Provisional Application No. 60/581,675 filed on Jun. 22, 2004 and Provisional Application No. 60/583,578 filed on Jun. 29, 2004, of which the complete subject matter of both is hereby incorporated by reference in their entirety.

BACKGROUND OF THE INVENTION

The present invention relates to diagnostic ultrasound methods and systems. In particular, the present invention relates to methods and systems for co-displaying multiple scan planes of a scanned object in real time.

Numerous ultrasound methods and systems exist for use in medical diagnostics. Various features have been proposed to facilitate patient examination and diagnosis based on ultrasound images of the patient. For example, certain systems offer a biplane imaging of an object, e.g. the human heart. One image of the biplane images may have a fixed orientation with respect to the transducer while the other image may be varied in relation to the fixed reference image. At least some systems with biplane imaging capability may rotate one image relative to the other, or may tilt one image relative to the other.

Heretofore, ultrasound methods and systems were unable to acquire multi-plane imaging for three or more imaging planes rapidly enough to be useful in real time display and analysis of the scanned multi-plane information. Also, conventional systems were unable to visually display the image displays with quantitative data, e.g. tissue velocity or strain rate.

A need exists for improved methods and systems that provide real time acquisition and display of three or more image planes of an object with optional display of quantitative data.

BRIEF DESCRIPTION OF THE INVENTION

In one embodiment, an ultrasound system is provided that includes a probe for successively acquiring ultrasound information from an object along at least three distinct scan planes. An example of a probe for the embodiment is a 2D array probe. The scan planes may intersect one another along an axis extending from the probe through the object. A memory is included for storing data slices corresponding to the at least three distinct scan planes based on the ultrasound information. Also included is a processor that accesses the memory to select and obtain the data slices and generates ultrasound images based on the data slices. A display is included for co-displaying the ultrasound images.

In another embodiment, an ultrasound method for successively acquiring ultrasound information from an object along at least three distinct scan planes is provided. Successive could be planewise whereby all scan information is collected for a first plane, then for a next plane, and so forth. In an alternative embodiment, successive could be vectorwise whereby scan information is collected in the order of vector 1 plane1, vector 2 plane 2, vector 3 plane 3, vector 2 plane 1, etc). In another embodiment, multi-line acquisition (MLA) may be used to collect scan information for a first plane, then a next plane, and so forth. In yet another embodiment, MLA may be done for plane 1, then for plane 2, then for plane 3, then repeating for plane 1, plane2, plane 3, until all data for all planes is collected. The embodiments of this invention should not be limited by the numerous possibilities for successive collection of scan data for all planes of a scanning pattern, e.g. biplane or tri-plane. The scan planes may intersect one another along an axis extending from the probe through the object. The method includes storing data slices corresponding to the at least three distinct scan planes based on the ultrasound information, generating ultrasound images based on the data slices, and co-displaying the ultrasound images.

DETAILED DESCRIPTION OF THE INVENTION

Figure 1:
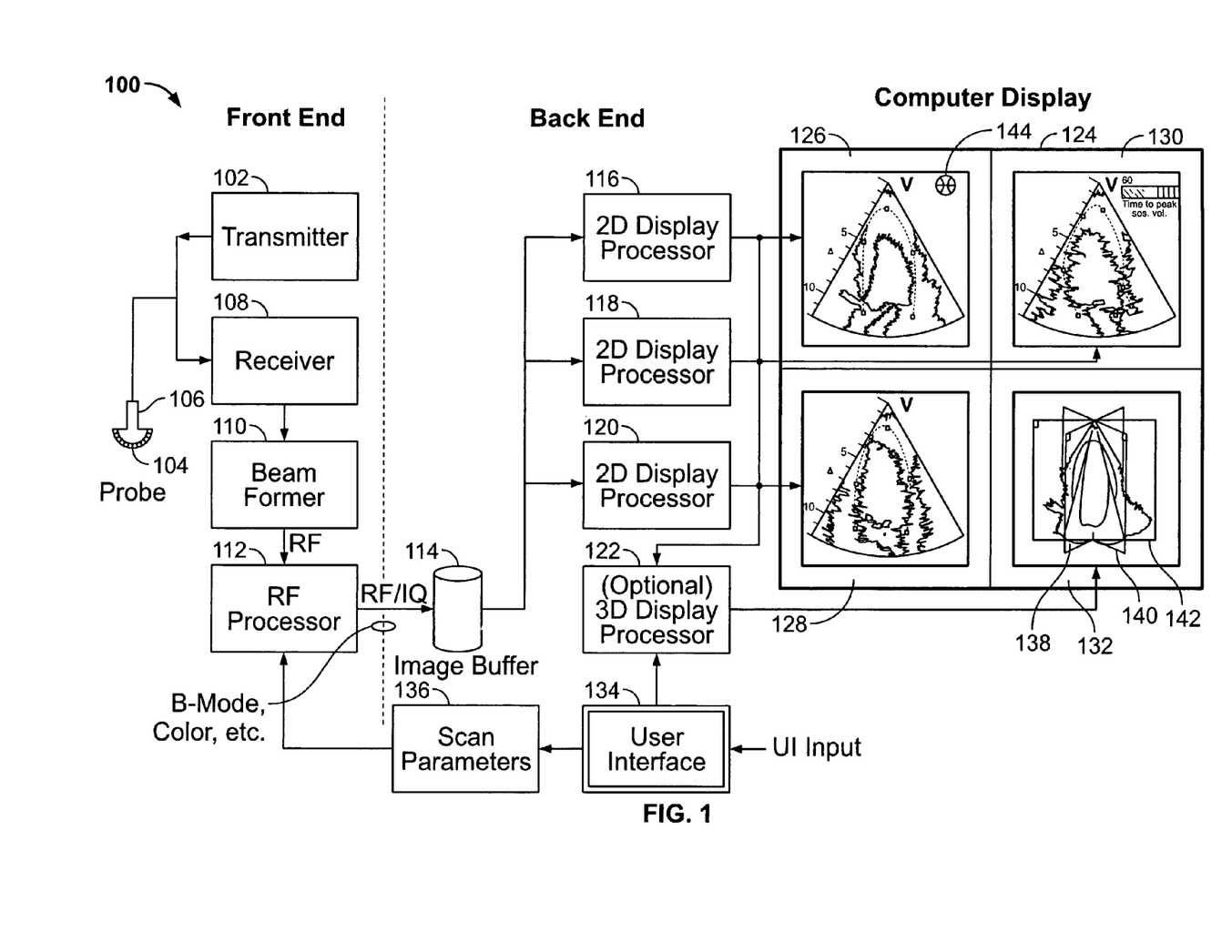
FIG. 1 is a block diagram of an ultrasound system formed in accordance with an embodiment of the present invention.

FIG. 1 is a block diagram of an ultrasound system 100 formed in accordance with an embodiment of the present invention. The ultrasound system 100 is capable of steering a soundbeam in 3D space, and is configurable to acquire information corresponding to a plurality of two-dimensional (2D) representations or images of a region of interest (ROI) in a subject or patient. One such ROI may be the human heart or the myocardium of a human heart. The ultrasound system 100 is configurable to acquire 2D images in three or more planes of orientation. The ultrasound system 100 includes a transmitter 102 that, under the guidance of a beamformer 110, drives a plurality of transducer elements 104 within an array transducer 106 to emit ultrasound signals into a body. The elements 104 within array transducer 106 are excited by an excitation signal received from the transmitter 102 based on control information received from the beamformer 110. When excited, the transducer elements 104 produce ultrasonic waveforms that are directed along transmit beams into the subject. The ultrasound waves are back-scattered from density interfaces and/or structures in the body, like blood cells or muscular tissue, to produce echoes which return to the transducer elements 104. The echo information is received and converted by the transducer elements 104 into electrical signals. The electrical signals are transmitted by the array transducer 106 to a receiver 108 and then passed to the beamformer 110. In the embodiment described, the beamformer 110 operates as a transmit and receive beamformer. In an alternative embodiment, the array transducer 106 is a 2D array with a sub-aperture rx beamforming inside the probe.

The beamformer 110 delays, apodizes and sums each electrical signal with other electrical signals received from the array transducer 106. The summed signals represent echoes from the ultrasound beams or lines. The summed signals are output from the beamformer 110 to an RF processor 112. The RF processor 112 may generate different data types, e.g. B-mode, color Doppler (velocity/power/variance), tissue Doppler (velocity), and Doppler energy, for multiple scan planes or different scanning patterns. For example, the RF processor 112 may generate tissue Doppler data for three (tri-plane) scan planes. The RF processor 112 gathers the information (e.g. I/Q, B-mode, color Doppler, tissue Doppler, and Doppler energy information) related to multiple data slices and stores the data information with time stamp and orientation/rotation information in an image buffer 114. Orientation/rotation information may indicate the angular rotation of one data slice with respect to a reference plane or another data slice. For example, in a tri-plane implementation whereby ultrasound information is acquired substantially simultaneously or consecutively within a short period of time (e.g. $\frac{1}{20}$ second) for three differently oriented scan planes or views, one data slice may be associated with an angle of 0 degrees, another with an angle of 60 degrees, and a third with an angle of 120 degrees. Thus, data slices may be added to the image buffer 114 in a repeating order of 0 degrees, 60 degrees, 120 degrees, . . . , 0 degrees, 60 degrees, and 120 degrees, . . . . The first and fourth data slices in the image buffer 114 have a first common planar orientation. The second and fifth data slices have a second common planar orientation and third and sixth data slices have a third common planar orientation.

Alternatively, instead of storing orientation/rotation information, a data slice sequence number may be stored with the data slice in the image buffer 114. Thus, data slices may be ordered in the image buffer 114 by repeating sequence numbers, e.g. 1, 2, 3, . . . , 1, 2, 3, . . . . In tri-plane imaging, sequence number 1 may correspond to a plane with an angular rotation of 0 degrees with respect to a reference plane, sequence number 2 may correspond to a plane with an angular rotation of 60 degree with respect to the reference plane, and sequence number 3 may correspond to a plane with an angular rotation of 120 degrees with respect to the reference plane. The data slices stored in the image buffer 114 are processed by 2D display processors 116, 118, and 120.

The 2D display processors 116, 118, and 120 operate alternatively and successfully in round-robin manner processing data slices from the image buffer 114. For example, the display processors 116, 118, and 120 may have access to all of the data slices in the image buffer 114, but are configured to operate upon data slices having one angular orientation. For example, the display processor 116 may only process data slices from the image buffer 114 associated with an angular rotation of 0 degrees or sequence number 1. Likewise, the display processor 118 may only process 60 degree oriented or sequence number 2 data slices, and the display processor 120 may only process 120 degree oriented or sequence number 3 data slices. Shown in a computer display 124 in a selected quadrant 126 is a graphic indicator 144 that indicates the relative angles between the planes.

The 2D display processor 116 may process a set of data slices having a common orientation from the image buffer 114 to produce a 2D image or view of the scanned object shown in the quadrant 126 of the computer display 124. The sequence of image frames played in the quadrant 126 may form a cine loop. Likewise, the display processor 118 may process a set of data slices from the image buffer 114 having a common orientation to produce a second different 2D view of the scanned object shown in a quadrant 130. The display processor 120 may process a set of data slices having a common orientation from the image buffer 114 to produce a third different 2D view of the scanned object shown in a quadrant 128.

For example, the data slices processed by the display processor 116 may produce an apical 2-chamber view of the heart to be shown in the quadrant 126. The data slices processed by the display processor 118 may produce an apical 4-chamber view of the heart to be shown in the quadrant 130. The display processor 120 may process data slices to form an apical long-axis view of the heart to be shown in the quadrant 128. All three views of the human heart may be shown simultaneously in real time in the three quadrants 126, 128, and 130 of the computer display 124.

A 2D display processor, for example the processor 116, may perform filtering of the data slice information received from the image buffer 114, as well as processing of the data slice to produce a processed image frame. Some forms of processed image frames may be B-mode data (e.g. echo signal intensity or amplitude) or Doppler data. Examples of Doppler data include color Doppler velocity data (CDV), color Doppler energy data (CDE), or Doppler Tissue data (DTI)). The display processor 116 may then perform scan conversion to map data from a polar to Cartesian coordinate system for display on a computer display 124.

Optionally, a 3D display processor 122 may be provided to process the outputs from the other 2D display processors 116, 118, and 120. The processor 122 may combine frames from the 3 views produced from 2D display processors 116, 118, and 120 to form a tri-plane view also referred to as a navigation image in a quadrant 132 of the computer display 124. The tri-plane view may show a 3D image, e.g. a 3D image of the human heart, aligned with respect to three intersecting planes 138, 140, and 142 of the tri-plane. The three planes 138, 140, and 142 may intersect at a common axis of rotation (not shown in FIG. 1) extending from the surface of the probe through the object.

A user interface 134 is provided which allows the user to input scan parameters 136. Examples of scan parameters include biplane, tri-plane, depth, scan angle, number of scan lines, rotation angle, and tilt angle with respect to the transducer surface. The scan parameters 136 allow the user to designate the number of scan planes desired. The scan parameters may allow for adjusting the depth and width of a scan of the object for each of the planes 138, 140, and 142 of the tri-plane. When performing simultaneous acquisition of data slices from the three scan planes 138, 140, and 142, the beamformer 110 in conjunction with the transmitter 102 controls the array transducer 106 to produce ultrasound beams that are focused along scan lines located within the three planes 138, 140, and 142 that extend through the object. Scan sequencing (beam order) successively collects scan information. Successive could be planewise whereby all scan information is collected for a first plane, then for a next plane, and so forth. In an alternative embodiment, successive could be vectorwise whereby scan information is collected in the order of vector 1 plane1, vector 2 plane 2, vector 3 plane 3, vector 2 plane 1, etc). In another embodiment, multi-line acquisition (MLA) may be used to collect scan information for a first plane, then a next plane, and so forth. In yet another embodiment, MLA may be done for plane 1, then for plane 2, then for plane 3, then repeating for plane 1, plane2, plane 3, until all data for all planes is collected. The embodiments of this invention should not be limited by the numerous possibilities for successive collection of scan data for all planes of a scanning pattern, e.g. biplane or tri-plane. The reflected ultrasound echoes are gathered to produce data slices that are stored in the image buffer 114. As the image buffer 114 is being filled by the RF processor 112, the image buffer 114 is being emptied by the 2D display processors 116, 118, and 120. The 2D display processors 116, 118, and 120 form the image frame data for viewing. The display of the three views in quadrants 126, 130, and 128, as well as an optional displaying of the combination of the three views in quadrant 132, is in real time. Real time display makes use of the data slices as soon as the data is available for display.

Figure 2:
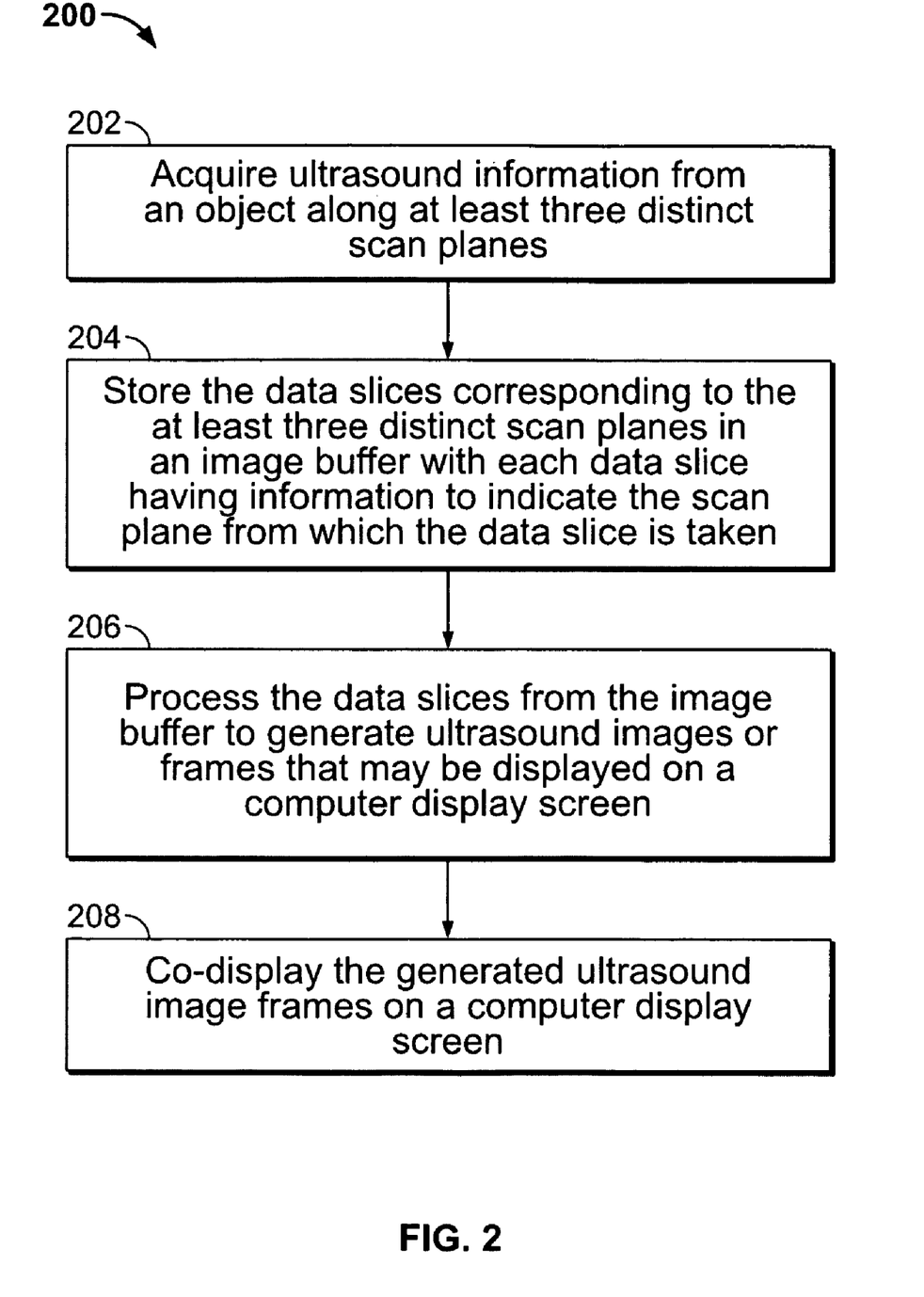
FIG. 2 is a flowchart of an exemplary method for acquiring, processing, and displaying in real time ultrasound tri-plane data.

FIG. 2 is a flowchart 200 of an exemplary method for acquiring, processing, and displaying in real time ultrasound data from multiple scan planes. Herein, an example embodiment of three planes (tri-plane) is used, but the present invention is not to be limiting in any way as to the number of scan planes along which data slices may be acquired. At 202, ultrasound data from an object is acquired successively from at least three distinct scan planes. The three scan planes may have a corresponding orientation to each other of 0 degrees, 60 degrees, and 120 degrees, and may intersect with each other along a common rotational axis that extends from the ultrasound probe surface through the object. The axis may be adjusted by the user changing scan parameters such that end points of the axis are repositioned. Adjusting the orientation of the rotational axis automatically adjusts the orientation of the three planes along the rotational axis. Also, through adjustment of scan parameters, one or more planes may be tilted with respect to the others. Data slices may simultaneously be acquired along the three distinct scan planes in less than 50 milliseconds.

The ultrasound information from the three planes may be at a predetermined time in a cycle of object motion. For example, the three planes may provide data slices for simultaneous views of the human heart at the end of the diastole phase of a heart cycle. The planes may be chosen to show a 2-chamber apical view, a 4-chamber apical view, and a apical long-axis view of the heart at a predetermined moment during the heart cycle.

As ultrasound information is acquired, it is organized into data slices by the beamformer 110 and stored at 204 into an image buffer 114 as 2D data slices. Each 2D data slice is stored with a time stamp and frame orientation or sequencing number relative to the other data slices. In the example of a tri-plane scan, the plane to which a 2D data slice is associated may be distinguished by a frame orientation angle, e.g. 0 degrees, 60 degrees, or 120 degrees, or by a sequence number of 1, 2, or 3. All the data slices of one orientation or sequence number are obtained from the same one of the three planes and may be used to produce a cine loop of images for real time display of the object from that plane or view. Data slices are stored into the image buffer 114 in an order of acquisition by orientation or sequence number. For example, if by sequence number, tri-plane data slices are stored in a repeating set of sequence numbers 1, 2, 3, 1, 2, 3, . . . . The image buffer 114 may be thought of as a ring in that once some predetermined number of cycles of data slices have been stored, the image buffer 114 may store further data slices by starting at the beginning of the buffer. In this way, the image buffer 114 wraps around on itself as a ring. As data slices are stored into the image buffer 114, the data slices are removed at a rate whereby the data slices are overwritten. Each sequence number or frame orientation may have a set of associated scan parameters. For example, data slices of sequence number 1 may have a predetermined scan width and depth while data slices of sequence number 2 may have a different predetermined scan width and depth. Data slices of sequence number 3 may have yet another different predetermined scan width and depth.

At 206, data slices are retrieved from the image buffer and processed by 2D image processors 116, 118, and 120. Each 2D image processor 116 may be programmed/dedicated to processing the data slices of a given orientation or sequence number. In the tri-plane example, three 2D image processors 116, 118, and 120 may be provided. One processor processes data slices with a sequence number 1, another processes data slices with a sequence number 2, and a third processes data slices with a sequence number 3. When a data slice is made available to a 2D image processor 116, the data slice is only processed by the 2D image processor 116 when the sequence number or orientation matches that of the 2D image processor 116.

Besides performing such functions as 2D spatial and temporal filtering of frame data, and scan conversion of the frames retrieved from the image buffer, a 2D image processor 116 may add color to the frame image in preparation for display of the image by a computer display. Color may be overlayed onto B-mode images by the 2D image processor 116 whereby the color may indicate, for example, the velocity of a tissue in a local area of the image. Depending on the mode of ultrasound data acquisition (e.g Color Doppler, Tissue Doppler, B-mode acquisition), the processed scan data may include tissue or blood velocity data from which velocity information may be derived. Color indications of velocity may be added to the ultrasound images by the 2D image processors 116-120. In order to achieve a higher frame rate, a 2D image processor 116 may not update the background (B-mode data) of an image frame for every frame. In order to achieve a higher frame rate of velocity data, scan sequencing may be such that only a partial B-mode frame (for example, one half-frame) is scanned for each color or tissue velocity frame. In one embodiment, a frame rate may be attained for tri-pane imaging of 15 color frames per second, or 25 black/white frames per second.

At 208, the image frames generated from the 2D image processors 116-120 are co-displayed. In addition to co-displaying the three images from a tri-plane scan, a velocity trace from a user selected area of at least one of the displayed images may be displayed. Through the user interface 134, a user may position a mouse cursor on the selected area of interest within one of the image displays, such as within one of the quadrants 126-132, and click the mouse to select and generate a velocity trace of that portion of the image over time. The velocity traces may be displayed on the computer display 124 as well as the images to which the traces correspond.

Figure 3:
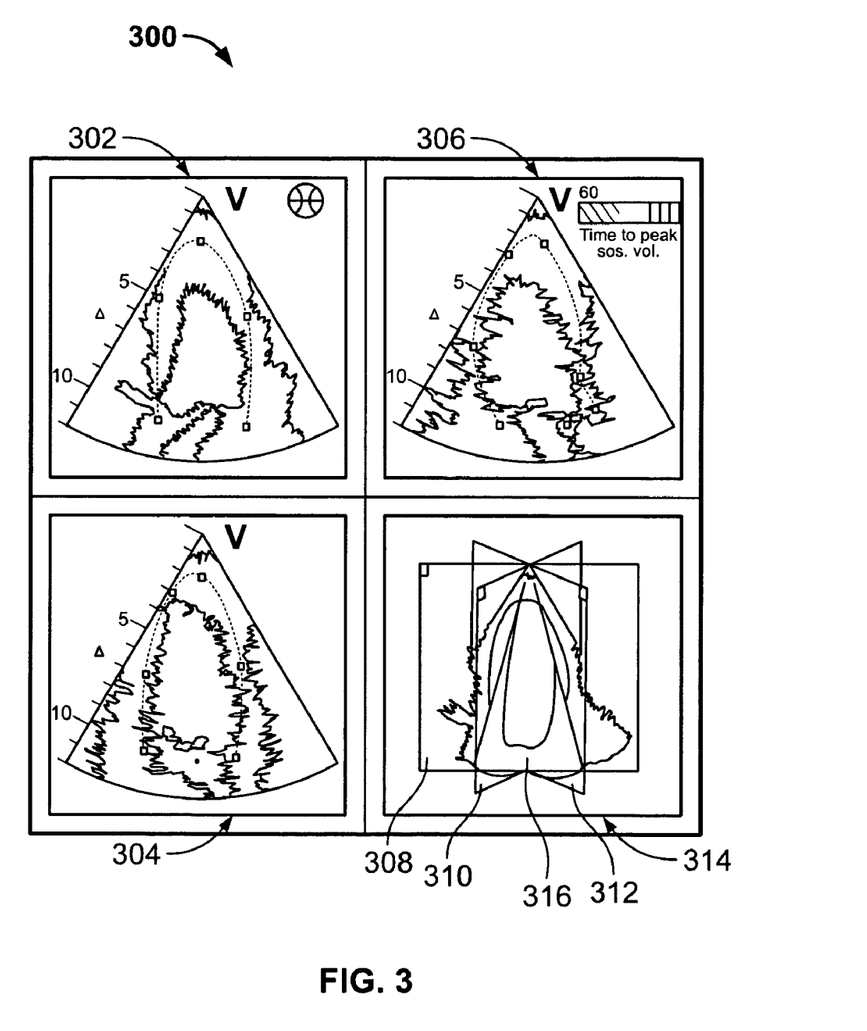
FIG. 3 is an exemplary screen display illustrating three co-displayed ultrasound images formed from three planes or views of the scanned object.

FIG. 3 is an exemplary screen display 300 illustrating three co-displayed ultrasound images 302, 304, and 306 formed from three corresponding views or planes 308, 310, and 312. Additionally shown is a 3D combined image 314 formed from the other 2D images 302, 304, and 306. The combined image 314 has a common rotational axis 316 along which the three planes 308, 310, and 312 intersect. Shown highlighted is image 306 wherein the user may have last mouse clicked and the corresponding plane 312 is highlighted in the combined image 314 designating to the user which plane the highlighted image 306 corresponds. If the user mouse clicks on the image 304, the image 304 becomes highlighted and the corresponding plane 310 in the compound image 314 is highlighted. In this manner, screen display 300 exhibits to the user the plane orientation from which scan data is taken to form the currently highlighted image. The three images 302, 304, and 306 show views of the scan object at about the same point in time due to simultaneous acquisition of the scan data for the three images 302, 304, and 306, simultaneous having the meaning defined herein. Because the images 302, 304, and 306 are displayed within one or two seconds of the data acquisition time of the corresponding scan data, the user is presented a real time image display while scanning is proceeding. The three images 302, 304, 306 may be of a patient's heart at a specific point in time of the heart beat or cycle. Alternatively, the three images 302, 304, and 306 may be showing continuous motion of a patient's heart while the heart beats. In one embodiment, a plane, e.g. plane 310, may be tilted (not shown in the figure) with respect to the other planes, as well as changing the angular rotation respective to the other planes, by the user modifying selected scan parameters associated with plane 310.

Figure 4:
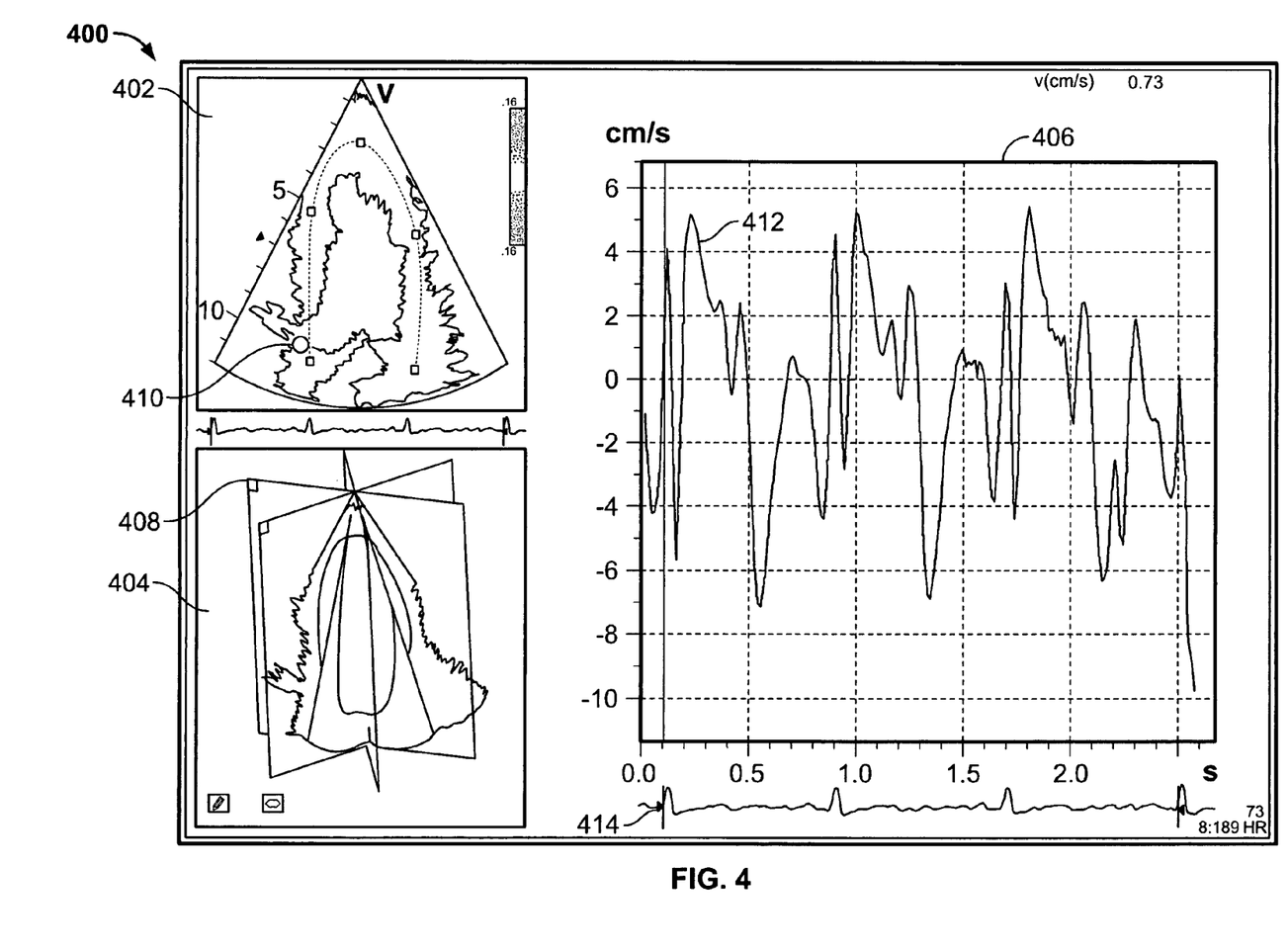
FIG. 4 is an exemplary screen shot illustrating a velocity trace of a selected region of interest (ROI) within one scan plane.

FIG. 4 is an exemplary screen display 400 illustrating a velocity trace 412 of a selected region of interest (ROI) 410 within one imaging plane 408 of a tri-plane ultrasound scan. A user may use a mouse to click on and select the ROI 410 within the imaged object of a planar view 402, for example, the ROI 410 selected may be in the basal septum area of the myocardium of a patient's heart. A tri-plane view 404 shows the three planes from which scan data is acquired and highlights and/or color matches the outline of the plane 408 to a color border of the planar view 402 to inform the user which plane of the tri-plane is displayed in the planar view 402. For example, the color border of the planar view 402 may be highlighted in yellow and the outline of the plane 408 in the tri-plane view 404 may be highlighted in yellow. The user may select when to start the velocity trace of the ROI 410 by mouse clicking a freeze button in the user interface (not shown in FIG. 4) In the example screen display 400, the user starts the velocity trace 412 at the end of the diastole phase 414 of the heart cycle. The velocity trace 412 shows velocity in cm/s (vertical axis) plotted against time in seconds (horizontal axis). Not visible in the black and white picture of FIG. 4, the velocity trace 412 is shown in a yellow color, which matches the color yellow used for the color border of the planar view 402 and the outline of the plane 408. The velocity trace is extracted from tissue velocity image (TVI) frames that are collected with a B-mode frame (1 to 3 or 1 to 4) A 2D processor combines the B-mode and TVI frames through filtering, scan converting and mixing. When mouse clicking the freeze button, a cine loop of the TVI and B-mode data is produced. Velocity is calculated from the TVI data and displayed in as the velocity trace 412 of the velocity display 406 of screen display 400.

Figure 5:
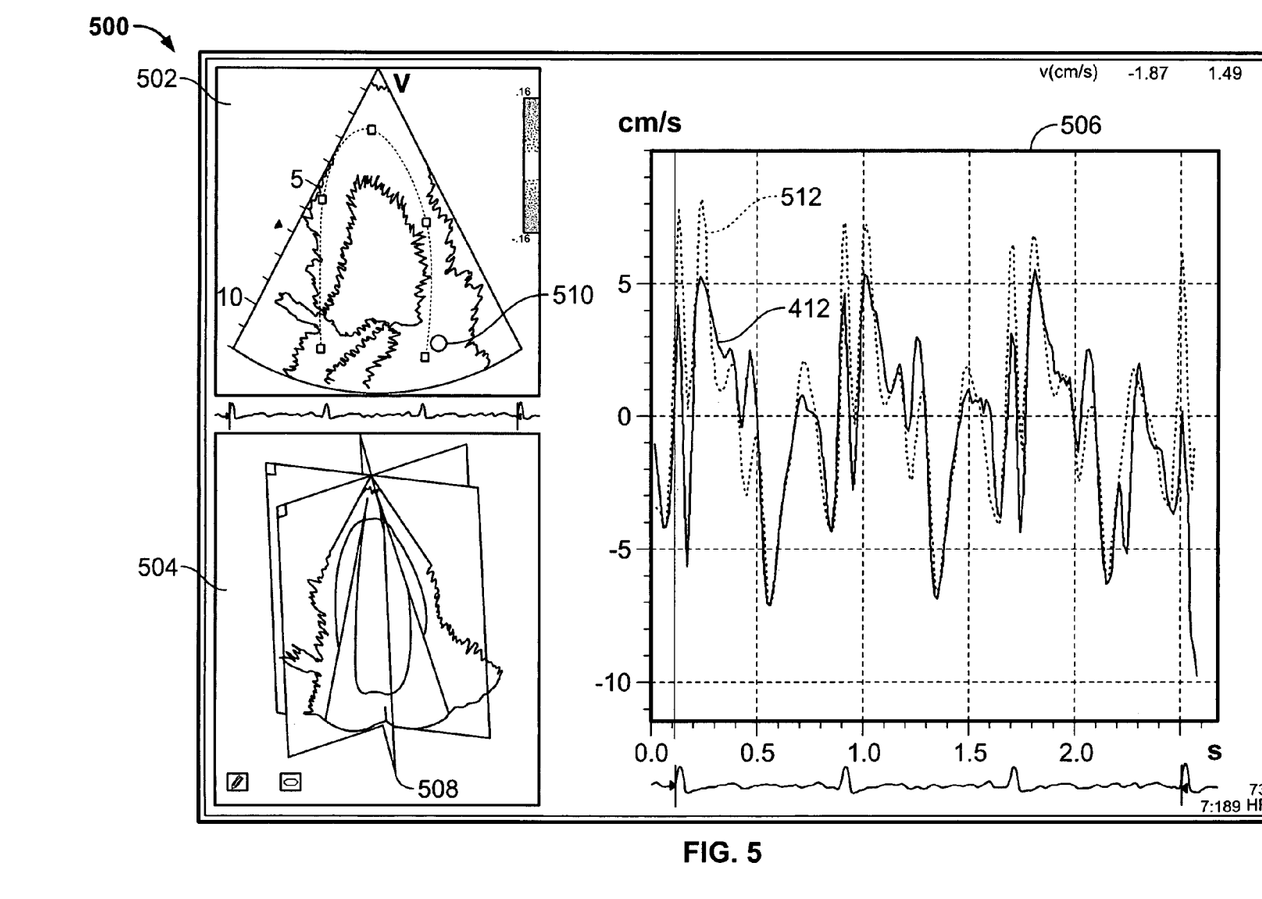
FIG. 5 is an exemplary screen shot illustrating a velocity trace of an ROI overlapping the velocity trace of FIG. 4.

FIG. 5 is an exemplary screen display 500 illustrating an overlapping of a velocity trace 512 of an ROI 510 with the velocity trace 412 of FIG. 4. Similar to the description related for FIG. 4, a user may use a mouse to click on and select the ROI 510 within the imaged object of a planar view 502, for example, the ROI 510 selected may be in the basal anterior area of the myocardium of a patient's heart. A tri-plane view 504 shows the three planes from which scan data is acquired and highlights and/or color matches the outline of the plane 508 to a color border of the planar view 502 to inform the user which plane of the tri-plane is displayed in the planar view 502. For example, the color border of the planar view 502 may be highlighted in blue and the outline of the plane 508 in the tri-plane view 504 may be highlighted in blue. Besides selecting the ROI 510, the user may also have selected the ROI 410 as described for FIG. 4. The user may select when to start the velocity trace by mouse clicking a freeze button in the user interface (not shown in FIG. 5) In the example screen display 500, the user starts the velocity traces 412 and 512 at the end of the diastole phase 414 of the heart cycle. The velocity trace 512 (in blue) is overlayed onto the velocity trace 412 (in yellow), both velocity traces showing velocity in cm/s (vertical axis) plotted against time in seconds (horizontal axis). Not visible in the black and white picture of FIG. 5, the velocity trace 512 is shown in a blue color, which matches the color blue used for the color border of the planar view 502 and the outline of the plane 508. When mouse clicking the freeze button, two cine loops of the TVI and B-mode data are produced, from which the two velocity traces 412 and 512 are calculated and displayed in the velocity display 506 of screen display 500.

Before selecting the freeze button to generate velocity traces, the user may select a plurality of ROIs for which velocities may be calculated and displayed. The user may optionally select one or more ROIs within a plane of the tri-plane, and/or select ROIs within multiple planes. When selecting the freeze button, velocity traces for all selected ROIs are generated and displayed, similar to the description provided for FIG. 4. Thus multiple ROIs may be selected to generate velocity traces, all being displayed within the same cycle of a heart beat. Such capability may be used to provide quantitative information, e.g. velocity or strain rate, about local and global function of the heart, e.g. timing and bulging.

Figure 6:
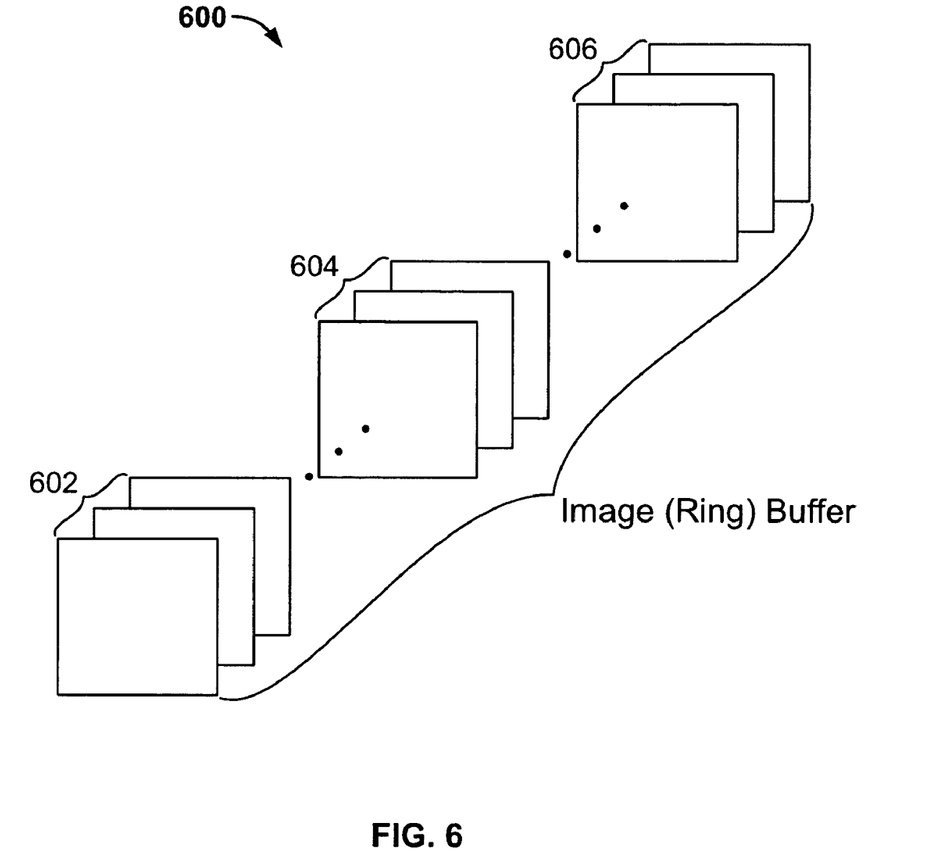
FIG. 6 is a diagram illustrating a ring buffer for buffering ultrasound data slices.

FIG. 6 is a diagram illustrating an image buffer 600 for buffering ultrasound data slices. Data slices are created from scan information and stored into the image buffer 600 as image sets, e.g. image sets 602, 604, and 606. An image set 602 is a plurality of data slices, the number of data slices in the image set 602 equal to the number of scan planes being scanned. In the example of a tri-plane scan, three data slices, one for each scan plane of the tri-plane, are included in the image set 602. Likewise, three data slices are included in each of the image sets 604 and 606. Although data slices are organized and ordered as image sets within the image buffer 600, individual data slices may be stored into and retrieved from the image buffer 600. As data slices are being generated and stored into the image buffer 600 by an RF processor, such as the RF processor 112 of FIG. 1, data slices are being retrieved/emptied from the opposite end of the image buffer 600 by 2D display processors, e.g. the display processors 116, 118, and 120 of FIG. 1. The image buffer 600 is also a ring buffer in that when the index that locates the storage location for a next data slice reaches the end of the image buffer 600, the index is reset to the beginning of the image buffer 600. The rate of processing of data slices from the image buffer 600 is equal to or greater than the rate at which data slices are stored into the image buffer. By maintaining this relation in the rates, the storage of data slices into the image buffer 600 does not overwrite data slices previously stored in the image buffer 600.

Exemplary embodiments of diagnostic ultrasound systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. An ultrasound system, comprising:
a probe configured to successively acquire ultrasound information from an object along at least three distinct scan planes intersecting one another to form a common rotational axis, said scan planes each formed from ultrasound signals emitted from a surface of the probe using electronic steering, said common rotational axis extending from the surface of the probe;
memory storing the ultrasound information acquired along the at least three distinct scan planes as data slices;
a processor accessing said memory to obtain said data slices and generating ultrasound images corresponding to said data slices, wherein the processor comprises a plurality of display processors processing different ones of the data slices to produce corresponding two-dimensional images for said data slices; and a display co-displaying said ultrasound images formed from said data slices and a tri-plane three-dimensional (3D) image representative of said at least three scan planes while the probe is scanning.

2. The ultrasound system of claim 1, wherein said probe automatically switches scanning between first, second and third scan planes upon completion of an acquisition along each of said first, second, and third scan planes without physically moving said probe relative to the object.

3. The ultrasound system of claim 1, wherein said memory includes a ring buffer that stores a series of said data slices, said series of data slices including multiple sets of data slices, each set containing data slices acquired along separate and distinct scan planes.

4. The ultrasound system of claim 1, wherein said display simultaneously co-displays at least three ultrasound images in adjacent quadrants of the display, said three ultrasound images corresponding to said at least three distinct scan planes.

5. The ultrasound system of claim 1, wherein said display simultaneously co-displays at least one ultrasound image and a navigation image representative of said at least three scan planes, wherein said navigation image includes said tri-plane 3D image.

6. The ultrasound system of claim 1, wherein said display displays a perspective view of said at least three ultrasound images intersecting one another along corresponding scan planes.

7. The ultrasound system of claim 1, wherein said processor performs at least one of temporal and spatial filtering upon said data slices.

8. The ultrasound system of claim 1, wherein said scan planes are oriented at predefined angles with respect to one another.

9. The ultrasound system of claim 1, wherein said probe includes a two dimensional array of transducer elements.

10. The ultrasound system of claim 1, wherein said memory stores at least one of a time stamp and an orientation stamp associated with each of said data slices, said time stamp identifying a point in time at which an associated data slice was obtained, said orientation stamp identifying an associated scan plane along which said data slice was obtained.

11. The ultrasound system of claim 1, wherein the display further displays quantitative data with the co-displayed ultrasound images, wherein the quantitative data includes one of a tissue velocity trace and strain rate information.

12. The ultrasound system of claim 1, wherein the plurality of display processors alternatively and successively process different ones of said data slices from the memory.

13. The ultrasound system of claim 1, wherein the processor is configured to acquire ultrasound information from an object along another three distinct scan planes intersecting one another about the common rotational axis and different from the three distinct scan planes.

14. The ultrasound system of claim 1, wherein the plurality of display processors are programmed to process different ones of the data slices corresponding to one of an orientation or a sequence number for the data slices to produce the corresponding two-dimensional images.

15. The ultrasound system of claim 1, wherein the plurality of display processors are programmed to process different ones of the data slices corresponding to the at least three distinct scan planes for generating individual images for each of said data slices.

16. The ultrasound system of claim 1, wherein the plurality of display processors comprise a first display processor processing a first one of said data slices, a second display processor processing a second one of said data slices and a third display processor processing a third one of said data slices to produce corresponding first, second and third images, where said first, second and third data slices correspond to the at least three distinct scan planes.

17. The ultrasound system of claim 16, wherein each of the first, second and third display processors process data slices for scan planes having different angular orientations.

18. The ultrasound system of claim 16, wherein each of the first, second and third display processors only process data slices from a corresponding image buffer associated with an angular orientation or sequence number for a distinct scan plane.

19. An ultrasound method, comprising:
successively acquiring ultrasound information from an object along at least three distinct scan planes each intersecting one another to form a common rotational axis, said scan planes formed from ultrasound signals emitted simultaneously from a surface of a probe using electronic steering, said common rotational axis extending from said probe through the object;
storing the ultrasound information acquired along the at least three distinct scan planes as data slices;
generating ultrasound images corresponding to said data slices using a plurality of dedicated image processors programmed to process predetermined different ones of the data slices; and
co-displaying said ultrasound images formed from said data slices and a tri-plane three-dimensional (3D) image representative of said at least three scan planes.

20. The ultrasound method of claim 19, further comprising automatically switching scanning between first, second and third scan planes upon completion of an acquisition along each of said first, second, and third scan planes without physically moving a probe relative to the object.

21. The ultrasound method of claim 19, wherein said storing includes utilizing a ring buffer to store a series of said data slices, said series of data slices including multiple sets of data slices, each set containing data slices acquired along separate and distinct scan planes.

22. The ultrasound method of claim 19, further comprising simultaneously co-displaying at least three ultrasound images in adjacent quadrants of the display, said three ultrasound images corresponding to said at least three distinct scan planes.

23. The ultrasound method of claim 19, further comprising simultaneously co-displaying at least one ultrasound image and a navigation image representative of said at least three scan planes, wherein said navigation image includes said tri-plane 3D image.

24. The ultrasound method of claim 19, further comprising displaying a perspective view of said at least three ultrasound images intersecting one another along corresponding scan planes.

25. The ultrasound method of claim 19, further comprising performing at least one of temporal and spatial filtering upon said data slices.

26. The ultrasound method of claim 19, wherein said scan planes are oriented at predefined angles with respect to one another.

27. The ultrasound method of claim 19, further comprising utilizing a two dimensional array of transducer elements to acquire said ultrasound information utilizing multi-line acquisition.

28. The ultrasound method of claim 19, further comprising storing at least one of a time stamp and an orientation stamp associated with each of said data slices, said time stamp identifying a point in time at which an associated data slice was obtained, said orientation stamp identifying an associated scan plane along which said data slice was obtained.

29. The ultrasound method of claim 19, further comprising separately processing data slices for each of said at least three scan planes having different angular orientations, using the plurality of dedicated image processors, to produce individual images for each of said data slices.

* * * * *